(12) United States Patent
Kanca, III (10) Patent No.: US 7,041,164 B2
(45) Date of Patent: May 9, 2006

(54) DENTAL ETCH SOLUTIONS

(75) Inventor: John A. Kanca, III, 264 Mirey Dam Rd., Middlebury, CT (US) 06762

(73) Assignee: John A. Kanca, III, Middlebury, CT (US)

( * ) Notice: Subject to any disclaimer, the term of this patent is extended or adjusted under 35 U.S.C. 154(b) by 413 days.

(21) Appl. No.: 10/323,865

(22) Filed: Dec. 18, 2002

(65) Prior Publication Data

US 2003/0175218 A1 Sep. 18, 2003

Related U.S. Application Data (60) Provisional application No. 60/358,883, filed on Feb. 21, 2002, provisional application No. 60/341,619, filed on Dec. 18, 2001.

(51) Int. Cl.
*C09K 13/04* (2006.01)
(52) U.S. Cl. .......................... 106/35; 433/216; 433/215; 252/79.1; 252/79.2; 252/79.4
(58) Field of Classification Search ................ 106/35; 252/79.1, 79.2, 79.4; 433/216, 215
See application file for complete search history.

(56) References Cited

U.S. PATENT DOCUMENTS 4,659,751 A * 4/1987 Bowen ................. 523/116
6,004,390 A * 12/1999 Pflug et al. ................ 106/35
6,458,869 B1 * 10/2002 Antonucci et al. .......... 523/118
6,592,372 B1 * 7/2003 Jia et al. ..................... 433/215

FOREIGN PATENT DOCUMENTS

| EP | 0321683 | 6/1989 |
| JP | 61176507 | 8/1986 |
| WO | WO 00/10478 | 3/2000 |
| WO | WO 03/051316 | 6/2003 |

OTHER PUBLICATIONS

International Search Report for PCT/US02/40700.
International Search Report for PCT/US2004/003711.

* cited by examiner

*Primary Examiner*—C. Melissa Koslow
(74) *Attorney, Agent, or Firm*—Dorsey & Whitney LLP; Scott D. Rothenberger (57) ABSTRACT

Etching compositions, curable compositions, packaged products and methods of use for the treatment of bone substrate, i.e., teeth, are described. The etch solutions generally include an inorganic acid, an organic acid and either a solvent, a surfactant or mixtures thereof. The curable composites include reactive monomers and crosslinking agents that are effective to adhere to the surface of the treated substrate. The methods of the invention provide the ability to modify a bone or bone-like surface so that the curable composition, such as an adhesive resin, can be used in combination with a restorative material.

24 Claims, 5 Drawing Sheets

THIS IMAGE SHOWS A TOOTH RESTORED WITH THE PRODUCT KNOWN AS "ONE-UP BOND," ANOTHER SELF-ETCH MATERIAL. THE ARROW POINTS TO THE CRITICAL AREA SHOWING DYE PENETRATION INTO THE TOOTH, INDICATING AN ADHESIVE FAILURE AT THAT MARGIN.

FIG. 3

THIS FIGURE SHOWS A TOOTH RESTORED WITH THE SELF-ETCH MATERIAL KNOW AS "PROMPT-L-POP." THE ARROW POINTS TO THE CRITICAL AREA IN WHICH THE DYE PENETRATES THE MARGIN, INDICATING ADHESIVE FAILURE

FIG. 4

THIS FIGURE SHOWS A TOOTH RESTORED WITH
THE SELF-ETCH MATERIAL KNOWN AS "CLEAFIL SE BOND."
THE ARROW POINTS TO THE CRITICAL AREA IN WHICH THE
DYE PENETRATES THE MARGIN, INDICATING ADHESIVE FAILURE.

FIG. 5

DENTAL ETCH SOLUTIONS

CROSS REFERENCE TO RELATED APPLICATIONS

The present application claims priority to U.S. Provisional Application No. 60/358,883, filed Feb. 21, 2002 and to U.S. Provisional Application No. 60/341,619, filed Dec. 18, 2001 which are hereby incorporated by reference.

FIELD OF THE INVENTION

The present invention relates to dental etching solutions, reactive monomeric based adhesive compositions, packaged pharmaceuticals that contain the etch solution and adhesive composition and methods for their use. More specifically, the present invention relates to a superior two step process, whereby an etch solution is applied to a tooth and subsequently causes the dentin to become receptive to adhesive compositions. After the reaction has occurred, the adhesive composition is applied to the tooth and the tooth is readied for a restorative material.

BACKGROUND OF THE INVENTION

The use of biomaterials as restorative materials, in both the dental and medical fields is growing and the requirements for such materials are often times difficult to achieve. Restorative materials such as amalgam or resin composites, are often used to repair dental tissues and bones.

For example, there has been considerable research devoted to the improvement of the adhesion of resins to hard tissues such as dentin or enamel. The adhesives are typically applied to the hard tissue after a pretreatment or etch of the tissue with an acidic solution. Various resin composites are available and generally suffer one or more disadvantages in providing a satisfactory bond between the tissue and the restorative material. Some of adhesive materials are designed to achieve higher bond strengths between tissue layers or the treated tissue and a restorative material, to improve physical properties, or the esthetics of the restored target substrate. Other desired properties of such adhesive composites are directed to their use and include ease in preparation and formulation for use under relatively humid conditions.

Typically an etch solution is utilized to remove the smear layer and demineralize the surface of the dental tissue. The etch solution can alter wettability or chemical reactivity of the pretreated dentin, prior to applying a bonding adhesive agent which is generally a polymerizable monomer. Polymerization of the bonding agent facilitates the bonding agent to adhere to the dentin. The interaction(s) between the bonding agent and the treated substrate is not entirely understood and is believed to be related to chemical, mechanical, interfacial diffusion or a combination of all three physical processes. Polymerization of most bonding adhesives provide an approximately 5 micron thick hybrid layer that is formed of part resin and part dentin. The depth and effectiveness of the penetration of the bonding agent is an important and often critical aspect to the adhesion between the bonding agent and substrate. This hybrid layer is believed to contain little or no apatite and the adhesion to dentin is believed to occur through collagen with the bonding agent.

Even though there has been continued research in the area of etching solutions and bonding agents, the techniques and/or products currently available for pretreating the dental or bone tissue or adhering a restorative material to the bone or dental tissue have limitations. For example, the bonding agents should effectively seal the dentin tubules to prevent post operative sensitivity and protect the pulp. Additionally, the bonds should last the lifetime of the restorative correction and be durable under a variety of conditions.

Therefore, a need exists for new compositions, solutions and methods which overcome one or more of the disadvantages of currently available products.

BRIEF SUMMARY OF THE INVENTION

The present invention provides a unique unexpectedly simple and easy to use bone, i.e., tooth, etch solution, a curable adhesive bonding composition, packaged products containing either or both of the compositions, and methods to use the compositions of the invention. The systems of the present invention can be self-cured or can be treated with light energy to facilitate curing.

The present invention provides distinct advantages over presently known etching/bonding systems. For example, the present etching solution is not required to be rinsed off, removed and/or dried prior to the application of a bonding composition. Most commercially available bonding systems require that the etch solution is rinsed off and the substrate dried prior to the application of the bonding resin. Alternatively, currently available bonding systems include both an etch solution and the bonding resin as a one component application. Often times, the one component application systems do not bond well to the bone substrate because the etch solution interferes with the ability of the bonding resin to adhere to the substrate.

In one embodiment, the present invention provides an etching solution capable of etching bone. In one aspect, the bone is teeth and more specifically, the substrate is dentin, enamel, gum, amalgam, metal, porcelain or plastic. The etching solution includes an inorganic acid, an organic acid, a surfactant, with the remainder being water. The inorganic acid is present in an amount of from about 1 to about 10 parts by weight. The organic acid is present in amount from about 0.01 to about 20 parts by weight. The surfactant is present in an amount from about 0.01 to about 10 parts by weight and the water is present in an amount to equal a total of 100 parts by weight of all components.

In another embodiment, the present invention provides etching solutions that include an inorganic acid, an organic acid, a solvent and water. The inorganic acid is present in an amount of from about 1 to about 10 parts by weight. The organic acid is present in amount from about 0.01 to about 20 parts by weight. The solvent is present in an amount from about 1 to about 50 parts by weight, with the water being present in an amount to equal a total of 100 parts by weight of all components.

In still another embodiment, the etching solution consists essentially of an inorganic acid, an organic acid, and water. In these compositions, the inorganic acid is present in an amount of from about 1 to about 10 parts by weight, the organic acid is present in an amount from about 0.01 to about 20 parts by weight with the water being present in an amount to equal a total of 100 parts by weight of all components.

In yet another embodiment of the invention, the etching solution consists essentially of an inorganic acid, an organic acid, a solvent and water. The inorganic acid is present in an amount of from about 1 to about 10 parts by weight and the organic acid is present in an amount from about 0.01 to about 20 parts by weight. The solvent is present in an amount from about 1 to about 50 parts by weight, with the water being present in an amount to equal a total of 100 parts by weight of all components.

Suitable components in the etching solution include, for example, nitric acid and succinic or citric acid, or combinations thereof, organic solvents such as acetone or lower weight alcohols, and/or various surfactants.

The present invention also pertains to curable composites that include (a) at least one ethylenically unsaturated functional monomer, (b) at least one polyethylenically unsaturated functional crosslinking monomer, (c) a (optionally) fluoride ion agent and (d) a solvent. More specifically, the ethylenically unsaturated monomer(s) of (a) is present in an amount of from about 0.5 to about 25 parts by weight. The polyethylenically unsaturated crosslinking monomer(s) of (b) is present in an amount from about 5 to about 40 parts by weight. The optional fluoride agent is present in an amount from about 0.5 to about 5 parts by weight, with the solvent being present in an amount to equal a total of 100 parts by weight of all components.

In certain embodiments, the functional monomer (a) of the curable composition is present in an amount between about 10 parts by weight and about 20 parts by weight. The polyethylenically unsaturated crosslinking monomer (b) is present in an amount between about 18 parts by weight and about 38 parts by weight, and the optional fluoride ion agent is present in an amount between about 0.1 parts by weight and about 10 parts by weight.

Suitable examples of functional monomer(s) (a) include, for example, hydroxyethylmethacrylate, hydroxypropylmethacrylate, and hydroxybutylmethacrylate. Exemplary polyethylenically unsaturated crosslinking monomer(s) (b) include a mixtures of PMGDM and bis-GMA. The optional fluoride ion agent is any source that provides a fluoride ion such as sodium fluoride.

In one particular aspect, the curable composition, the functional monomer (a) is hydroxyethylmethacrylate, the polyethylenically unsaturated crosslinking monomer (b) is a mixture of PMGDM and bis-GMA, and the fluoride ion agent is sodium fluoride. More particularly, the functional monomer (a) is present in an amount of about 15 parts by weight, the first polyethylenically unsaturated crosslinking monomer, PMGDM, is present in an amount of about 20 parts by weight, the second polyethylenically unsaturated crosslinking monomer, bis-GMA, is present in an amount of about 8 parts by weight and the optional sodium fluoride is present in an amount between about 1 and 2 parts by weight.

The curable composition generally includes a photoinitiator system. The photoinitiator system includes a light-sensitive initiator and a polymerization accelerator. A suitable light-sensitive initiator is camphorquinone (CQ) and a suitable polymerization accelerator is ethyl N,N-dimethyl-4-aminobenzoic acid or ethyldimethylaminobenzoic acid (EDMAB).

The present invention further provides packaged formulations of the etch solutions, the curable compositions, combinations thereof.

The present invention also provides method to use the etch solutions, alone or in combination with the curable compositions of the invention. It should be understood that the etch solutions of the present invention can be used with those commercially available bonding resins. The method of the invention involves applying an effective amount of an etching solution to the substrate. The etch solution can be any of the solutions described herein, and for example, can include an inorganic acid, an organic acid, a solvent and water. The excess etching solution is removed such that the substrate remains moist. This can be easily accomplished by touching an absorbent material to the surface and blotting the excess from the surface. Thereafter, a curable composite is applied to the moist substrate, i.e., a tooth.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The present invention provides a unique unexpectedly simple and easy to use bone, i.e., tooth, etch solution, a curable adhesive bonding composition, packaged products containing either or both of the compositions, and methods to use the compositions of the invention. The present invention provides distinct advantages over presently known etching/bonding systems as described throughout the specification.

In one embodiment, the present invention provides an etching solution capable of etching bone. In one aspect, the bone substrate is a tooth and more specifically, the substrate is dentin, enamel, gum, amalgam, metal, porcelain or plastic. The etching solution includes an inorganic acid, an organic acid, a surfactant, with the remainder of the solution being water.

The inorganic acid is present in the etch solution in an amount of from about 1 to about 10 parts by weight. Suitable ranges of inorganic acid include from about 2 to about 9 parts by weight, about 4 to about 8 parts by weight, and about 5 to about 7 parts by weight, i.e. about 6 to about 8 parts by weight. The organic acid is present in the etch solution in amount from about 0.01 to about 20 parts by weight. Additional suitable ranges of the organic acid include from about 1 to about 15 parts by weight, 4 to about 12 parts by weight and from about 6 to about 10 parts by weight. The surfactant in the etch solution is present in an amount from about 0.01 to about 10 parts by weight, from about 0.1 to about 5 parts by weight or from about 0.5 to about 2.5 parts by weight. The water in the etch solution is present in an amount to equal a total of 100 parts by weight of all components.

In another embodiment, the present invention provides etching solutions that include an inorganic acid, an organic acid, a solvent and water. The inorganic acid and the organic acid are present in the parts by weight as described above. The solvent is present in an amount from about 1 to about 50 parts by weight, from about 5 to about 40 parts by weight or from about 10 to about 30 parts by weight. The water in the etch solution is present in an amount to equal a total of 100 parts by weight of all components.

In an embodiment, the present invention provides etching solutions that include an inorganic acid, an organic acid, an ethylenically unsaturated monomer and water. The inorganic acid and the organic acid are present in the parts described above. The ethylenically unsaturated monomer is present in an amount from about 0.1 to about 10 parts by weight, from about 1.0 to about 5 parts by weight, or from about 2 to about 4 parts by weight, e.g., from about 2 to about 7 parts by weight, e.g., 2.5 parts by weight. The water in the etch solution is present in an amount to equal a total of 100 parts by weight of all components.

In still another embodiment, the etching solution consists essentially of an inorganic acid, an organic acid, and water. In these compositions, the inorganic acid and organic acid are present in the parts by weight as described above with the water being present in an amount to equal a total of 100 parts by weight of all components.

In yet another embodiment of the invention, the etching solution consists essentially of an inorganic acid, an organic acid, a solvent and water. The inorganic acid, the organic acid and the solvent are present in the parts by weight as described above, with the water being present in an amount to equal a total of 100 parts by weight of all components.

In an embodiment, the present invention provides etching solutions that consists essentially of an inorganic acid, an organic acid, an ethylenically unsaturated monomer and water. The inorganic acid, the organic acid ethylenically unsaturated monomer are present in an amount as described above, with the water being present in an amount to equal a total of 100 parts by weight of all components.

In still yet another aspect, the invention pertains to etching solutions that include, or consist essentially of, nitric acid and an organic solvent.

It should be understood that throughout the specification, the etching solution can be utilized on any bone or bone-like substrate that includes, but is not limited to, apatite and hydroxyapatite. Bone is a complex mineralizing system composed of an inorganic or mineral phase, an organic matrix phase, and water. The inorganic mineral phase is composed mainly of crystalline calcium phosphate salts while the organic matrix phase consists mostly of collagen and other noncollagenous proteins.

The phrases "etching solution" or "etch solution" are recognized in the art and are intended to include the compositions of the invention that superficially dissolve or modify bone or bone-like substrates. For example, in the case of teeth, the etch solution removes the smear layer and facilitates demineralization of the surface of the dental tissue.

As described above, the etch solutions of the present invention include several components. Suitable inorganic acids include nitric acid, sulfuric acid, hydrochloric acid, phosphoric acid and mixtures thereof. In one aspect, the inorganic acid is nitric acid. Nitric acid is generally available as a 70 percent aqueous solution and is utilized at this concentration throughout this application. Sulfuric acid, hydrochloric acid and phosphoric acid are also available as 95–98 percent, 37 percent and 85 percent aqueous solutions, respectively, and are utilized at these concentrations throughout the application. Where noted as parts by weight, this refers to using the concentrated inorganic acid, at the respective commercial concentration, on a weight basis.

It should be noted that commercially available etch solutions that contain phosphoric acid do not work well in dental applications if the solution is not first rinsed from the substrate to which it is applied. This is due to the precipitation of calcium phosphate from the etch solution that is generated by the reaction of phosphoric acid with the calcium of the bone substrate. The present invention avoids such precipitation by either utilizing a different inorganic acid or by using an organic solvent, surfactant and/or organic acid which inhibit the deposition of calcium phosphate onto the cleaned bone substrate surface.

Suitable organic acids include lactic acid, pyruvic acid, glycolic acid, chloroacetic acid, dichloroacetic acid, trichloroacetic acid, cyanoacetic acid, tartaric acid, succinic acid, glutaric acid, maleic acid, fumaric acid, malonic acid, citraconic acid, ortho-phthalic acid, meta-phthalic acid, para-phthalic acid, citric acid, tricarballyic acid, 1,3,5-pentanetricarboxylic acid and trimellitic acid and mixtures thereof. Other suitable organic acids include 2-acrylamido-2-methylpropane sulfonic acid, benzenesulfonic acid, benzoic acid, bromoacetic acid, 10-camphorquinonesulfonic acid, 10-camphorsulfonic acid, dibromoacetic acid, 2,4-dinitrophenol, formic acid, fumaric acid, 2-hydroxy-4-methoxybenzophenone-5-sulfonic acid, maleic-acid, 2-naphthalene sulfonic acid, nitric acid, oxalic acid, p-nitrophenol, phenol, phosphorous acid esters (such as 2,2'-bis(a-methacryloxy-b-hydroxypropoxyphenyl)propane diphosphonate (Bis-GMA diphosphonate), dibutyl phosphite, di-2-ethylhexyl phosphate, di-2-ethyl-hexyl phosphite, hydroxyethyl methacrylate monophosphate, glyceryl dimethacrylate phosphate, glyceryl-2-phosphate, glyceryiphosphoric acid, methacryloxyethyl phosphate, pentaerythritol triacrylate monophosphate, pentaerythritol trimethacrylate monophosphate, dipentaerythritol pentaacrylate monophosphate, and dipentaerythritol pentamethacrylate monophosphate), toluene sulfonic acid, tribromoacetic acid, trifluoroacetic acid, trifluoromethanesulfonic acid, and trihydroxybenzoic acid. Mixtures of such acids can be used if desired. In one aspect, the organic acid is succinic acid or citric acid. In another aspect, the succinic acid concentration is between about 1.0 and about 3.0 parts by weight.

The term "surfactant" is recognized in the relevant art to include those compounds which modify the nature of surfaces, e.g. reducing the surface tension of water. Surfactants are generally classified into four types: cationic (e.g. modified onium salts, where part of the molecule is hydrophilic and the other consists of straight or branches long hydrocarbon chains such as hexadecyltrimethyl bromide), anionic, also known as amphiphatic agents (e.g., alkyl or aryl or alkylarylsulfonates, carboxylates, phosphates), nonionic (e.g., polyethylene oxides, alcohols) and ampholytic or amphoteric (e.g. dodecyl-beta-alanine, such that the surfactant contains a zwitterionic group). One or more surfactants can be used in the present invention.

Cationic surfactants useful as surface tension reducing agents in the present invention include long chain hydrocarbons which contain quaternarized heteroatoms, such as nitrogen. Suitable cationic surfactants include quaternary ammonium compounds in which typically one of the groups linked to the nitrogen atom is a C12–C18 alkyl group and the other three groups are short chained alkyl groups.

Anionic surfactants (amphiphatic agents) are characterized by a single lipophilic chain and a polar head group which can include sulfate, sulfonate, phosphate, phosphonate and carboxylate. Exemplary compounds include linear sodium alkyl benzene sulfonate (LAS), linear alkyl sulfates and phosphates, such as sodium lauryl sulfate (SLS) and linear alkyl ethoxy sulfates. Additional examples of anionic surfactants include substituted ammonium (e.g., mono-, di-, and tri-ethanolammonium), alkali metal and alkaline earth metal salts of C6–C20 fatty acids and rosin acids, linear and branched alkyl benzene sulfonates, alkyl ether sulfates, alkane sulfonates, olefin sulfonates, hydroxyalkane sulfonates, fatty acid monoglyceride sulfates, alkyl glyceryl ether sulfates, acyl sarcosinates, acyl N-methyltaurides, and alkylaryl sulfonated surfactants, such as alkylbenzene sulfonates.

Nonionic surfactants do not dissociate but commonly derive their hydrophilic portion from polyhydroxy or polyalkyloxy structures. Suitable examples of polyhydroxy (polyhydric) compounds include ethylene glycol, butylene glycol, 1,3-butylene glycol, propylene glycol, glycerine, 2-methyl-1,3-propane diol, glycerol, mannitol, corn syrup, beta-cyclodextrin, and amylodextrin. Suitable examples of polyalkyloxy compounds include diethylene glycol, dipropylene glycol, polyethylene glycols, polypropylene glycols and glycol derivatives.

Other suitable nonionic surfactants include other linear ethoxylated alcohols with an average length of 6 to 16 carbon atoms and averaging about 2 to 20 moles of ethylene oxide per mole of alcohol; linear and branched, primary and secondary ethoxylated, propoxylated alcohols with an average length of about 6 to 16 carbon atoms and averaging 0–10 moles of ethylene oxide and about 1 to 10 moles of propylene oxide per mole of alcohol; linear and branched alkylphenoxy (polyethoxy) alcohols, otherwise known as ethoxylated alkylphenols, with an average chain length of 8 to 16 carbon atoms and averaging 1.5 to 30 moles of ethylene oxide per mole of alcohol; and mixtures thereof.

Additionally, suitable nonionic surfactants include polyoxyethylene carboxylic acid esters, fatty acid glycerol esters, fatty acid and ethoxylated fatty acid alkanolamides. Block copolymers of propylene oxide and ethylene oxide, and block polymers of propylene oxide and ethylene oxide with propoxylated ethylene diamine are also included as acceptable nonionic surfactants. Semi-polar nonionic surfactants like amine oxides, phosphine oxides, sulfoxides, and their ethoxylated derivatives are included within the scope of the invention.

Suitable amphoteric and zwitterionic surfactants which contain an anionic water-solubilizing group, a cationic group and a hydrophobic organic group include amino carboxylic acids and their salts, amino dicarboxylic acids and their salts, alkylbetaines, alkyl aminopropylbetaines, sulfobetaines, alkyl imidazolinium derivatives, certain quaternary ammonium compounds, certain quaternary phosphonium compounds and certain tertiary sulfonium compounds.

Examples of anionic, nonionic, cationic and amphoteric surfactants that are suitable for use in the present invention are described in Kirk-Othmer, Encyclopedia of Chemical Technology, Third Edition, Volume 22, pages 347–387, and McCutcheon's Detergents and Emulsifiers, North American Edition, 1983, both of which are incorporated herein by reference.

Typical concentration ranges of surfactant that are useful in the present etch solutions are from about 0.01 parts by weight to about 10 parts by weight, from about 0.1 parts by weight to about 5 parts by weight, and from about 0.5 parts by weight to about 2.5 parts by weight.

The etch solutions of the present invention can further include an aldehyde component and in particular a dialdehyde. Suitable aldehydes include formaldehyde, compounds which release formaldehyde, acetaldehyde, propionaldehyde and butyraldehyde and mixtures thereof. Glutaraldehyde is a dialdehyde that is suitable for such use. Suitable ranges of aldehyde or dialdehyde vary from about 0.1 to about 5 parts by weight, from about 0.5 to about 2.5 parts by weight, and from about 1 to about 2 parts by weight.

The terms "solvent" or "organic solvent" are recognized in the art and are intended to mean those components, other than water, that can be added to the etch solutions of the invention to help solubilize the components and aid in the evaporation of the etch solution from the substrate surface after application. Suitable solvents include those which are known to be pharmacologically acceptable for treatment of bone tissue. These solvents include dimethyl sulfoxide, ethyl acetate, alcohols and ethers such as methanol, ethanol, propanol, butanol, ethylene glycol, propanediol, butanediol, pentanediol, butenediol, glycerin, trimethylolpropane, hexanetriol, allyl alcohol, diethylene glycol, diethylene glycol monomethyl ether, diethylene glycol monoethyl ether, triethylene glycol, triethylene glycol monomethyl ether, tetraethylene glycol, propylene glycol, dipropylene glycol, tripropylene glycol, 2-methoxyethanol, 2-ethoxyethanol, 2-(methoxyethoxy) ethanol, 2-isopropoxyethanol, 2-butoxyethanol, 1-methoxy-2-propanol, 1-ethoxy-2-propanol, dipropylene glycol, dipropylene glycol monomethyl ether, tripropylene glycol monomethyl ether, glycerine ether and the like, as well as ketones such as acetone, methyl ethyl ketone and the like and mixtures thereof. The solvent is present in an amount from about 1 to about 50 parts by weight, from about 5 to about 40 parts by weight or from about 10 to about 30 parts by weight.

It should be understood that all values, including non-whole values (integers), inclusive, within the ranges of all concentrations (parts by weight) provided throughout this specification are considered individually. That is, it is within the discretion of the operator to choose any percentage within the ranges provided for any of the metal salts as described herein. Therefore, the ranges provided are not limiting in terms of more narrow ranges and individual values that are encompassed by the parameters of the ranges identified.

The etch solutions of the present invention can also further include one or more ethylenically unsaturated functional monomers as detailed below. Suitable concentration ranges are from about 5 to about 30 percent, from about 5 to about 20 percent, and from about 7.5 to about 15 percent. In particular, small amounts of such monomers facilitate in the handling and drying aspects of the etch solution. In particular, ethyleneglycol methacrylate phosphate (Aldrich Chemical Company product number 46,333-7) has been found to facilitate both the handling and drying of the etch solution in the above-identified concentration ranges.

The present invention also pertains to curable composites that include (a) at least one ethylenically unsaturated functional monomer, (b) at least one polyethylenically unsaturated functional crosslinking monomer, (c) (optional) a fluoride ion agent and (d) a solvent, with the solvent being present in an amount to equal a total of 100 parts by weight of all components.

The ethylenically unsaturated monomer(s) present in the curable composite resins of the invention (a) is present in an amount of from about 0.5 to about 25 parts by weight, from about 10 to about 20 parts by weight, and from about 12 to about 17 parts by weight.

The phrase "ethylenically unsaturated monomer" includes those reactive agents that include a double bond that can undergo polymerization with other monomers to form a polymeric matrix. The polymerization can be between like monomers or mixtures of monomers. Additionally, the monomers that are ethylenically unsaturated can further react with polyethylenically unsaturated functional crosslinking monomers to form crosslinked networks.

Suitable ethylenically unsaturated monomers, include, but are not limited to ethyleneglycol acrylate phosphate (and methacrylate), 2-hydroxyethylacrylate (HEA), 2-hydroxyethylmethacrylate (HEMA), 2- and 3-hydroxypropylacrylate and methacrylate, 1,3 and 2,3-dihydroxypropylacrylate and methacrylate, acrylic acid, methacrylic acid, 2-trimethylammonium ethylmethacrylic chloride, 2-acrylamido-2-methylpropane-sulfonic acid, acrylamide, methacrylamide, 2-hydroxyethylacrylamide and methacrylamide, N,N-bis(2-hydroxyethyl)acrylamide and methacrylamide, N-alkyl-N-hydroxyethyl acrylamides and methacrylamides, 2- and 3-hydroxypropylacrylamide and methacrylamide, methacrylamidopropyltrimethylammonium chloride, gylcerol monomethacrylate and monoacrylate, various reactive ethylenically unsaturated phosphates, and mixtures thereof. It is considered that where an acrylate monomer is suitable the methacrylate analog will likewise be suitable.

The polyethylenically unsaturated crosslinking monomer(s) of (b) is present in an amount from about 5 to about 40 parts by weight, from about 10 to about 30 parts by weight, and from about 15 to about 25 parts by weight, i.e., about 20 parts by weight.

The phrase "polyethylenically unsaturated functional crosslinking monomer" is recognized in the art and is intended to include those crosslinking agents that have two or more reactive double bonds present within the monomeric backbone. The degree of unsaturation provides the ability to polymerize with other crosslinking agent(s) as well as ethylenically unsaturated monomers to form a network of polymerized material.

Suitable crosslinking monomers include, for example, 2-hydroxypropyl-1,3-diacrylate and dimethacrylate, 3-hydroxypropyl-1,2-diacrylate and dimethylacrylate, pentaerythritol diacrylate and dimethacrylate, polyethyleneglycol (400) diacrylate and dimethacrylate, glycerol dimethacrylate and diacrylate and pentaerythritol trimethacrylate and triacrylate, the reaction product of pyromellitic dianhydride with glycerol dimethacrylate (PMGDM), addition product of 2-hydroxyethyl (meth)acrylate and pyromellitic dianhydride (PMDM), 2,2'-bis[4-(3-methacryloxy-2-hydroxy propoxy)-phenyl]-propane (bis-GMA) and mixtures thereof. In certain aspects of the invention, PMGDM and bis-GMA are preferred.

The term "fluoride agent" is recognized in the art and is intended to include those reagents that provide a fluoride ion. Suitable reagents include fluoride salts, such as sodium fluoride, potassium fluoride, ammonium fluoride, cetyl ammonium fluorides, such as cetyl trialkylammonium fluorides, and mixtures thereof.

The fluoride agent, optionally, is present in an amount from about 0.5 to about 5 parts by weight, from about 1 to about 3 parts by weight, and from about 1 to about 2 parts by weight.

In certain embodiments, the functional monomer (a) of the curable composition is present in an amount between about 10 parts by weight and about 20 parts by weight. The polyethylenically unsaturated crosslinking monomer (b) is present in an amount between about 18 parts by weight and about 38 parts by weight, and the fluoride ion agent is present in an amount between about 0.1 parts by weight and about 10 parts by weight.

Suitable examples of functional monomer(s) (a) include, for example, hydroxyethylmethacrylate, hydroxypropylmethacrylate, and hydroxybutylmethacrylate. Exemplary polyethylenically unsaturated crosslinking monomer(s) (b) include a mixtures of PMGDM and bis-GMA. The optional fluoride ion agent is any source that provides a fluoride ion such as sodium fluoride.

In one particular aspect, the curable composition, the functional monomer (a) is hydroxyethylmethacrylate, the polyethylenically unsaturated crosslinking monomer (b) is a mixture of PMGDM and bis-GMA, and the optional fluoride ion agent is sodium fluoride. More particularly, the functional monomer (a) is present in an amount of about 15 parts by weight, the first polyethylenically unsaturated crosslinking monomer, PMGDM, is present in an amount of about 20 parts by weight, the second polyethylenically unsaturated crosslinking monomer, bis-GMA, is present in an amount of about 8 parts by weight and the sodium fluoride is present in an amount between about 1 and 2 parts by weight.

The curable composition generally includes a photoinitiator system. The photoinitiator system includes a light-sensitive initiator and a polymerization accelerator. A suitable light-sensitive initiator is camphorquinone and a suitable polymerization accelerator is ethyl N,N-dimethyl4-aminobenzoic acid or N,N-dimethylaminoethyl methacrylate.

Since most of the polymerization reactions which ethylenically unsaturated compounds undergo, particularly acrylate and methacrylate compounds, proceed by a free radical mechanism, a free radical initiator is generally included in the monomer system. Any free radical initiator which is substantially non-toxic in the amounts employed in the composition; which does not react adversely with either the polymeric matrix, once formed, and cures within a few minutes is acceptable. The free radical initiator may be of the chemical type (redox system) in which a peroxide initiator and a polymerization accelerator react at ambient temperatures to initiate the polymerization of the monomer system. Alternatively, a photoinitiator system is used in which light, such as ultraviolet light, but preferably the visible portion of the spectrum, is employed as the energy source to stimulate the free radical initiator.

Examples of such chemical initiators include hydroperoxides, peresters or peroxides such as benzoyl peroxide, or amines, tertiary aromatic amines, such as N,N-dimethyl toluidine can be used. Suitable photoinitiators include benzyl 2,3-butanedione, phenyl-1,2-propandione, and camphorquinone (CQ).

Suitable light sources that are effective to cause photoinitiation to occur include halogen, laser, plasma and LED sources. The amount of energy required, is that amount which is sufficient to initiate a photochemical reaction such that polymerization of the ethylenically unsaturated components is started or enhanced. One skilled in the art can determine the amount of light required to cause such reaction to occur and many light systems are commercially available.

The present invention further provides packaged formulations of the etch solutions, the curable compositions, combinations thereof.

For example, the present invention provides a packaged formulation having an etching solution including an inorganic acid, an organic acid, a surfactant and water. The concentrations of the inorganic acid, the organic acid, the surfactant and the water are as provided throughout the present specification. Instructions are provided for the application of the etching solution to a bone substrate, i.e., a tooth, such that the substrate is conditioned for further treatment with a curable composition. The instructions provide the length of time to apply the solution, how to remove the excess solution, and how to bond a restorative material, e.g., a fixture, to the treated substrate.

The present invention further provides packaged formulations that include an etching solution having an inorganic acid, an organic acid, a solvent and water. The concentrations of the inorganic acid, the organic acid, the solvent and the water are as provided throughout the present specification. Instructions are provided for the application of the etching solution to a bone substrate, i.e., a tooth, such that the substrate is conditioned for further treatment with a curable composition. The instructions provide the length of time to apply the solution, how to remove the excess solution, and how to bond a restorative material to the treated substrate.

The present invention also provides packaged formulations that consist essentially of an etching solution with an inorganic acid, an organic acid, and water. The concentrations of the inorganic acid, the organic acid, and the water are as provided throughout the present specification. Instructions are provided for the application of the etching solution to a bone substrate as described previously and throughout the specification.

The present invention further provides packaged formulations of an etching solution that consist essentially of an inorganic acid, an organic acid, a solvent and water. The concentrations of the inorganic acid, the organic acid, the solvent and the water are as provided throughout the present specification. Instructions are provided for the application of the etching solution to a bone substrate as described previously and throughout the specification.

The present invention also provides packaged formulations that include an etching solution that has an inorganic acid, an organic acid, an ethylenically unsaturated monomer and water. The concentrations of the inorganic acid, organic acid and ethylenically unsaturated monomer are as provided throughout the present specification. Instructions are provided for the application of the etching solution to a bone substrate as described throughout the specification.

The present invention further provides packaged formulations that consist essentially of an etching solution that has an inorganic acid, an organic acid, an ethylenically unsaturated monomer and water. The concentrations of the inorganic acid, organic acid and ethylenically unsaturated monomer are as provided throughout the present specification. Instructions are provided for the application of the etching solution to a bone substrate as described throughout the specification.

In another aspect, packaged formulations are provided that include a first container having an etching solution and a second container having a curable composition. The etching solution includes an inorganic acid, an organic acid, a surfactant and water. The concentrations of the inorganic acid, the organic acid, the surfactant and the water are as provided throughout the present specification. Instructions are provided for the application of the etching solution to a bone substrate, i.e., a tooth, as described previously and throughout the specification.

The second container having the curable composite includes (a) at least one ethylenically unsaturated functional monomer; (b) at least one polyethylenically unsaturated functional crosslinking monomer; (c) (optional) a fluoride ion agent; and (d) a solvent. The concentrations of (a), (b), (c) and (d) are as provided throughout the present specification. Instructions are also provided for the application of the curable composite to the bone substrate, i.e., a tooth, such that the substrate is conditioned for further treatment with a restorative material.

In still another aspect, packaged formulations are provided that include a first container having an etching solution and a second container having a curable composition. The etching solution includes an inorganic acid, an organic acid, a solvent and water. The concentrations of the inorganic acid, the organic acid, the solvent and the water are as provided throughout the present specification. Instructions are provided for the application of the etching solution to a bone substrate as described previously and throughout the specification.

The second container having the curable composite includes (a) at least one ethylenically unsaturated functional monomer; (b) at least one polyethylenically unsaturated functional crosslinking monomer; (c) (optional) a fluoride ion agent; and (d) a solvent. The concentrations of (a), (b), (c) and (d) are as provided throughout the present specification. Instructions are also provided for the application of the curable composite to the bone substrate, i.e., a tooth, such that the substrate is conditioned for further treatment with a restorative material.

In another aspect, packaged formulations are provided that include a first container having an etching solution and a second container having a curable composition. The etching solution consists essentially of an inorganic acid, an organic acid and water. The concentrations of the inorganic acid, the organic acid and the water are as provided throughout the present specification. Instructions are provided, for the application of the etching solution to a bone substrate, i.e., a tooth, as described previously and throughout the specification.

The second container having the curable composite includes (a) at least one ethylenically unsaturated functional monomer; (b) at least one polyethylenically unsaturated functional crosslinking monomer; (c) a (optional) ion agent; and (d) a solvent. The concentrations of (a), (b), (c) and (d) are as provided throughout the present specification. Instructions are also provided for the application of the curable composite to the bone substrate, i.e., a tooth, such that the substrate is conditioned for further treatment with a restorative material.

In still another aspect, packaged formulations are provided that include a first container having an etching solution and a second container having a curable composition. The etching solution consists essentially of an inorganic acid, an organic acid, solvent and water. The concentrations of the inorganic acid, the organic acid, the solvent and the water are as provided throughout the present specification. Instructions are provided for the application of the etching solution to a bone substrate, i.e., a tooth, as described previously and throughout the specification.

The second container having the curable composite includes (a) at least one ethylenically unsaturated functional monomer; (b) at least one polyethylenically unsaturated functional crosslinking monomer; (c) (optional) a fluoride ion agent; and (d) a solvent. The concentrations of (a), (b), (c) and (d) are as provided throughout the present specification. Instructions are also provided for the application of the curable composite to the bone substrate, i.e., a tooth, such that the substrate is conditioned for further treatment with a restorative material.

Alternatively, the etch solution of the first container includes an inorganic acid, an organic acid, an ethylenically unsaturated monomer and water and/or a solvent. The concentrations of the inorganic acid, organic acid, the ethylenically unsaturated monomer, water, and/or solvent, are as provided throughout the present specification. Instructions are provided for the application of the etching solution to a bone substrate, i.e., a tooth, as described previously and throughout the specification.

In another embodiment, the etch solution of the first container consists essentially of an inorganic acid, an organic acid, an ethylenically unsaturated monomer and water and/or a solvent. The concentrations of the inorganic acid, organic acid, the ethylenically unsaturated monomer, water, and/or solvent, are as provided throughout the present specification. Instructions are provided for the application of the etching solution to a bone substrate, i.e., a tooth, as described previously and throughout the specification.

The containers that can be used for the packaged products are those that are generally commercially available. Any container suitable for retaining the liquids can be used that does not react with the solution(s). The container can be a reusable bottle, as known in the art, a single use bottle or pouch. The container can be collapsible, such as those foil packets known in the art. In certain embodiments, it is advantageous to provide a container that does not permit light to penetrate through the bottle. The solutions can be stored at or below room temperature, so that the container should be to withstand temperatures below room temperature. Bottles or packets prepared from polyethylene or polypropylene are suitable as well as those aluminized foil packets prepared from various terephthalates.

The present invention also provides methods to use the etch solutions, alone or in combination with the curable compositions of the invention. It should be understood that the etch solutions of the present invention can be used with those commercially available bonding resins. The method of the invention involves applying an effective amount of an etching solution to the substrate. The etch solution can be any of the solutions described herein, and for example, can include an inorganic acid, an organic acid, a solvent and water. The excess etching solution is removed from the substrate such that the substrate remains moist. This can be easily accomplished by touching an absorbent material to the surface and blotting the excess from the surface. Thereafter, a curable composite is applied to the moist substrate, i.e., a tooth. The curable composites of the packaged formulations and methods which follow can further include photoinitiator systems as described throughout the specification.

The present invention also provides methods for adhering a material to a bone substrate, i.e., a dental substrate. The methods generally include applying an effective amount of an etching solution that includes an inorganic acid, an organic acid, a surfactant and water to a substrate, removing excess etching solution from the substrate such that the substrate remains moist and applying a curable composite to the moist substrate. The curable composite can be exposed to a light source that emits an effective amount of energy to cure the composite. A restorative material can be adhered to the composite thereafter.

The concentrations of the inorganic acid, the organic acid, the surfactant, the water and the components of the curable composition are as provided throughout the present specification.

In another aspect, the invention provides methods for adhering a material to a bone substrate, i.e., a dental substrate. The methods generally include applying an effective amount of an etching solution that includes an inorganic acid, an organic acid, a solvent and water to a substrate, removing excess etching solution such that the substrate remains moist and applying a curable composite to the moist substrate. The curable composite can be exposed to a light source that emits an effective amount of energy to cure the composite. A restorative material can be adhered to the composite thereafter.

The concentrations of the inorganic acid, the organic acid, the solvent, the water and the components of the curable composition are as provided throughout the present specification.

The present invention further provides methods for adhering a material to a bone substrate, i.e., a dental substrate. The methods generally include applying an effective amount of an etching solution that consists essentially of an inorganic acid, an organic acid, a surfactant and water to a substrate, removing excess etching solution such that the substrate remains moist and applying a curable composite to the moist substrate. The curable composite can be exposed to a light source that emits an effective amount of energy to cure the composite. A restorative material can be adhered to the composite thereafter.

The concentrations of the inorganic acid, the organic acid, the surfactant, the water and the components of the curable composition are as provided throughout the present specification.

In still another aspect, the invention provides methods for adhering a material to a bone substrate, i.e., a dental substrate. The methods generally include applying an effective amount of an etching solution that consists essentially of an inorganic acid, an organic acid, a solvent and water to a substrate, removing excess etching solution such that the substrate remains moist and applying a curable composite to the moist substrate. The curable composite can be exposed to a light source that emits an effective amount of energy to cure the composite. A restorative material can be adhered to the composite thereafter.

The concentrations of the inorganic acid, the organic acid, the solvent, the water and the components of the curable composition are as provided throughout the present specification.

In an alternative embodiment, the invention provide methods for adhering a material to a bone substrate as described throughout the specification. The methods generally include application of an effective amount of an etch solution that includes an inorganic acid, an organic acid, an ethylenically unsaturated monomer, water and/or a solvent to a substrate, removing the excess etch solution such that the substrate remains moist and application of a curable composite to the moist substrate. The curable composite can be exposed to a light source that emits an effective amount of energy to cure the composite. A restorative material can be adhered to the composite thereafter.

The concentrations of the inorganic acid, the organic acid, the solvent, the water and the components of the curable composition are as provided throughout the present specification.

In an alternative embodiment, the invention provide methods for adhering a material to a bone substrate as described throughout the specification. The methods generally include application of an effective amount of an etch solution that consists essentially of an inorganic acid, an organic acid, an ethylenically unsaturated monomer, water and/or a solvent to a substrate, removing the excess etch solution such that the substrate remains moist and application of a curable composite to the moist substrate. The curable composite can be exposed to a light source that emits an effective amount of energy to cure the composite. A restorative material can be adhered to the composite thereafter.

The concentrations of the inorganic acid, the organic acid, the solvent, the water and the components of the curable composition are as provided throughout the present specification.

The phrase "effective amount of an etching solution" or "effective amount of a dental etching solution" is that amount required to modify the surface architecture of the bone substrate. Not to be limited by theory, it is believed that the etching solution removes proteins, lipids, and other foreign materials from the surface of the substrate and penetrates into the substrate. The surface and the penetrated substrate area are cleaned and modified such that they are receptive toward further modification, i.e., a curable composite where reactive functionality such as ethylenic bonds can attach to the modified material. A skilled artisan can readily determine the amount of etch solution to apply to the substrate, however, only enough of the solution is required so as to wet the surface and keep it moist as the surface is modified during rubbing.

The phrases "removing excess etching solution" or "removing excess dental etching solution" is intended to mean that a sufficient amount of the etching solution is removed from the substrate so that the surface remains wetted, i.e., moist. This can be accomplished by a variety of ways, including but not limited to, contacting the wet surface with an absorbent material, i.e., a cotton swab or tissue, passing a stream of air over the surface, and other methods known in the art. Ideally, enough etch solution should remain so that the surface of the substrate remains moist and does not become dry.

In an exemplary method, the substrate material is cleaned with isopropyl alcohol, rinsed with water and dried for at least 3 seconds. 1–2 drops of the etch solution are placed in an open well receptacle and a cotton or foam pellet is contacted to the solution. The moistened applicator is contacted to the substrate such that the area to be treated is wetted. The applicator is gently agitated with the solution against the surface for at least about 10 to about 30 seconds, i.e., from about 10 to about 30 seconds, from about 10 to about 20 seconds, or from about 10 to about 15 seconds.

Generally, the etch solution is allowed to remain on the substrate surface for approximately 10 to about 30 seconds, i.e., from about 10 to about 20 seconds, or from about 10 to about 15 seconds. During this time, the applicator is then pressed against an absorbent material, such as a patient napkin or to a facial tissue, to remove most of the liquid from the applicator. The wetted surface is contacted to the partially dried applicator to remove the excess etch solution while leaving the surface visibly moist. Alternatively, the wetted surface can be partially dried by passing compressed air over the treated surface area. Ideally, the preparation should not be allowed to dry. There is no requirement to rinse the etch solution from the surface before any further applications are done.

After the etching treatment is complete, from about 1 to about 3 coats of an adhesive resin, such as those that are available commercially or those described within the present application, can be applied directly over the moist conditioned preparation with a suitable applicator, such as a brush. The adhesive resin is dried gently, for about 5–8 seconds to facilitate evaporation of the solvent. After the surface is dried, the surface should appear to be "shiny," if not, additional resin adhesive should be applied. The adhesive resin is then light-cured for about 10 seconds. Optionally, a restorative material can be applied to the adhesively treated surface to continue the procedure. However, depending upon what therapeutic treatment is intended, the adhesive resin can serve as a protectant covering and no further restorative treatment may be necessary.

For example, the etching/adhesive system can be used to seal enamel/dentin prior to restoration with light-cured or self-cured composite materials. Indirect Restorations are also encompassed by the present invention and include those preparations when using a light-cured, self-cured or dual-cured composite cement or glass ionomer or resin-modified glass ionomer cement. The methods and compositions of the invention can also be useful for desensitization to treat hypersensitive and/or exposed root surfaces. Additionally, the methods and compositions of the invention can be used to bond in a post and core.

Restorative materials applicable for use with the present invention include those known in the art. Composite materials, synthetic bone materials, bone-like apatite and hydroxyapatite materials are well suited for use with the compositions and methods of the invention. Suitable examples of dental restoratives include composite filling materials, inlays, onlays, crown, bridges, ceramics, veneers and Maryland bridges.

The invention is further illustrated by the following examples which in no way should be construed as being further limiting. The contents of all references, pending patent applications and published patent applications, cited throughout this application, including those referenced in the background section, are hereby incorporated by reference. It should be understood that the models used throughout the examples are accepted models and that the demonstration of efficacy in these models is predictive of efficacy in humans.

Figure 1:
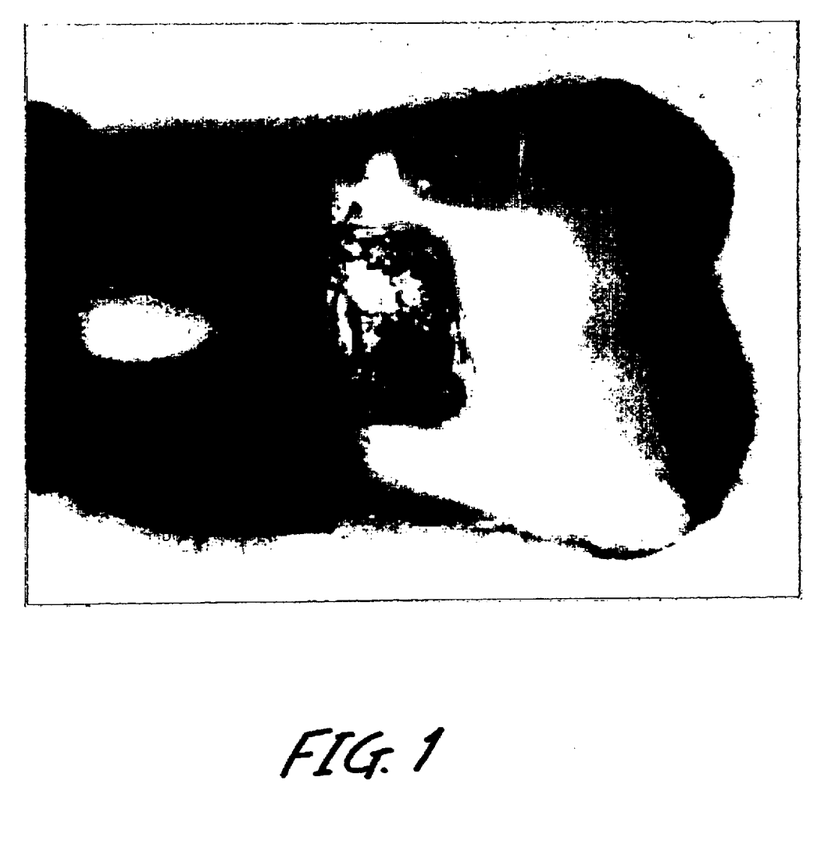
FIG. 1 is a cross sectional photograph of a tooth treated with an etch solution of the present invention followed by subsequent treatment with an adhesive bonding composition of the invention. The tooth was placed in 0.5% fushin dye for 24 hours. The photograph demonstrates that no dye penetrated along the margins treated with the etch and bonding composite of the invention.

FIG. 1 is a cross sectional photograph of a tooth treated with an etch solution of the present invention followed by subsequent treatment with an adhesive bonding composition of the invention. The tooth was placed in 0.5% fushin dye for 24 hours. The photograph demonstrates that no dye penetrated along the margins treated with the etch and bonding composite of the invention.

Figure 2:
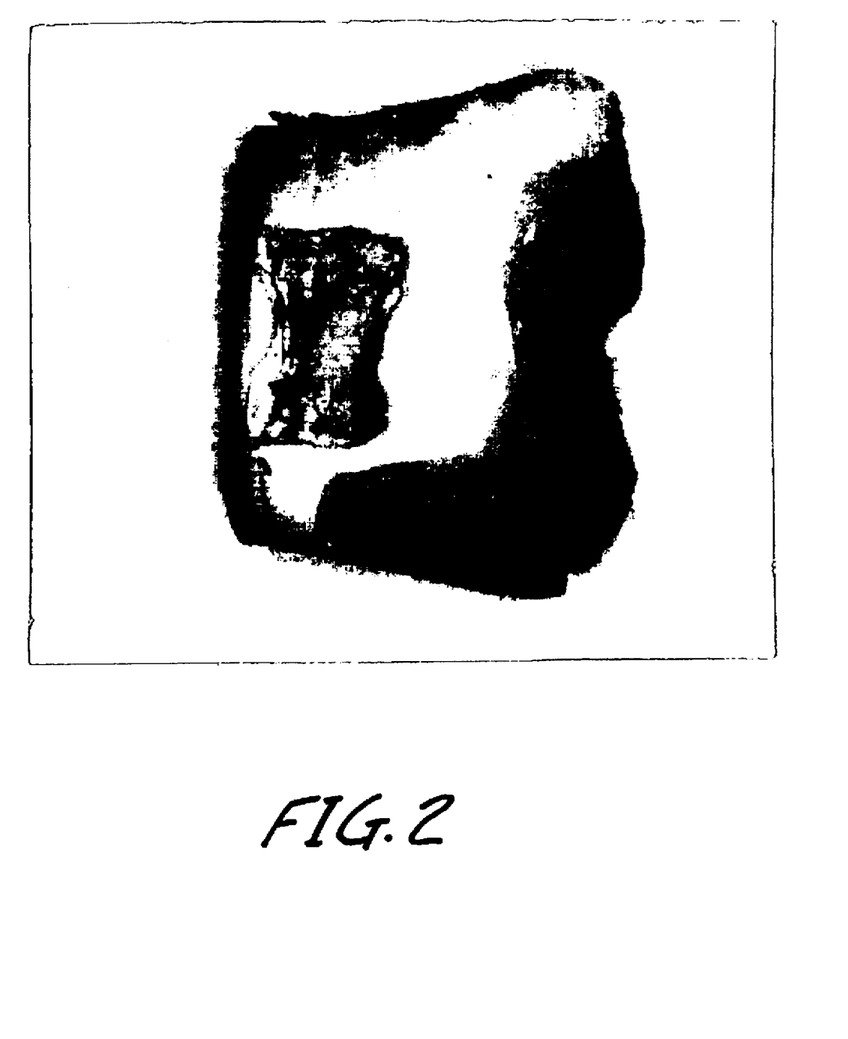
FIG. 2 is a second cross sectional photograph of the tooth depicted in FIG. 1 with the root of the tooth removed.

FIG. 2 is a second cross sectional photograph of the tooth depicted in FIG. 1.

Figure 3:
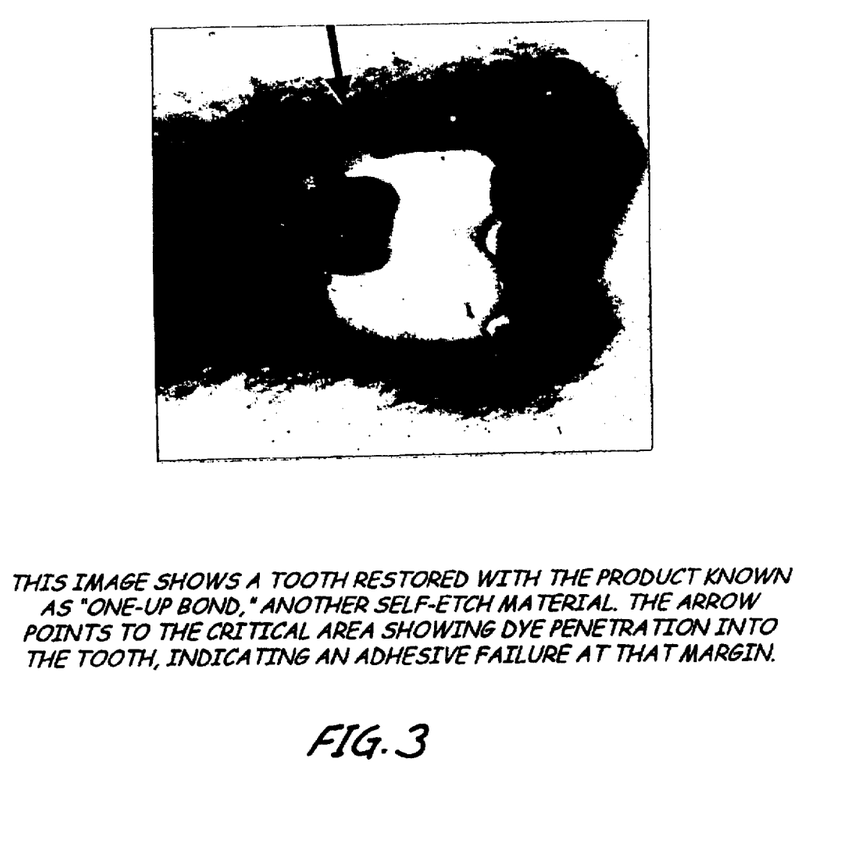
FIG. 3 is a cross sectional photograph of a tooth treated with "One Up Bond", a commercially available etch/bonding system. The arrow points to the critical area showing dye penetration into the tooth, indicating an adhesive failure at the margins of the treatment.

FIG. 3 is a cross sectional photograph of a tooth treated with "One Up Bond", a commercially available etch/bonding system. One Up Bond contains a proprietary phosphate ester referred to as MAC-10 and is available from J. Moriat USA, Inc., 9 Mason, Irvine, Calif. 92618. The arrow points to the critical area showing dye penetration into the tooth, indicating an adhesive failure at the margins of the treatment.

Figure 4:
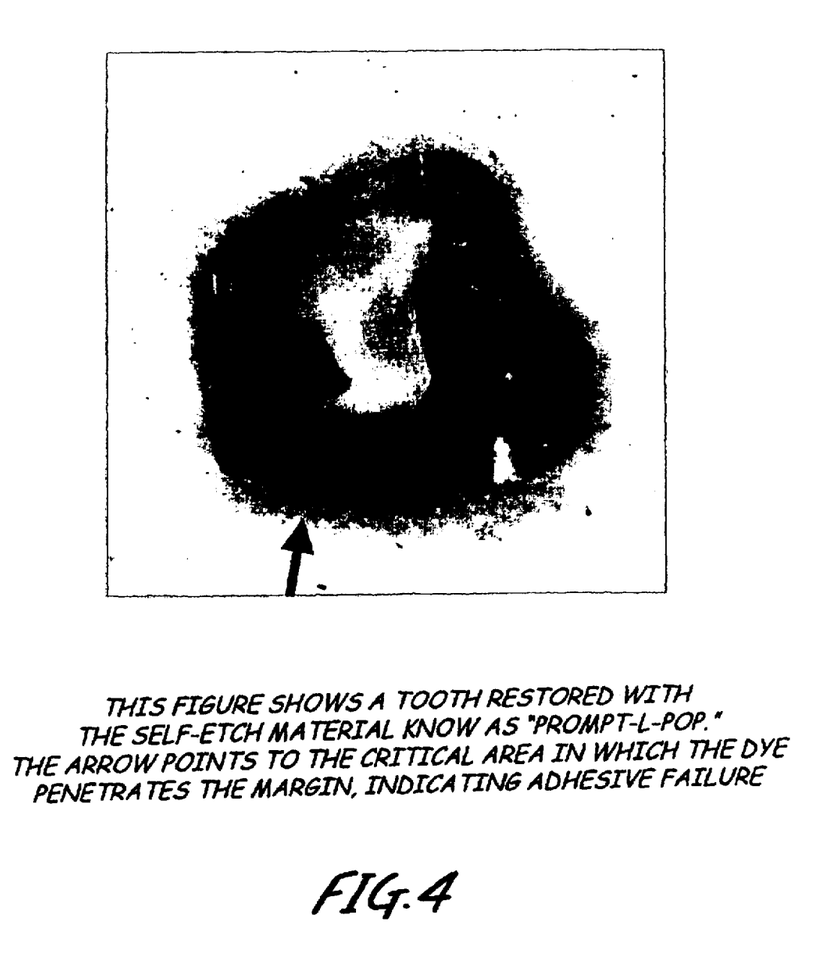
FIG. 4 is a cross sectional photograph of a tooth treated with "Prompt-L-Pop, a commercially available etch/bonding system. The arrow points to the critical area showing dye penetration into the tooth, indicating an adhesive failure at the margins of the treatment.

FIG. 4 is a cross sectional photograph of a tooth treated with "Prompt-L-Pop, a commercially available etch/bonding system. Prompt-L-Pop contains phosphonic acids and is available from 3M ESPE Dental Products, P.O. Box 33275, St. Paul, Minn. 55133-3275. The arrow points to the critical area showing dye penetration into the tooth, indicating an adhesive failure at the margins of the treatment.

Figure 5:
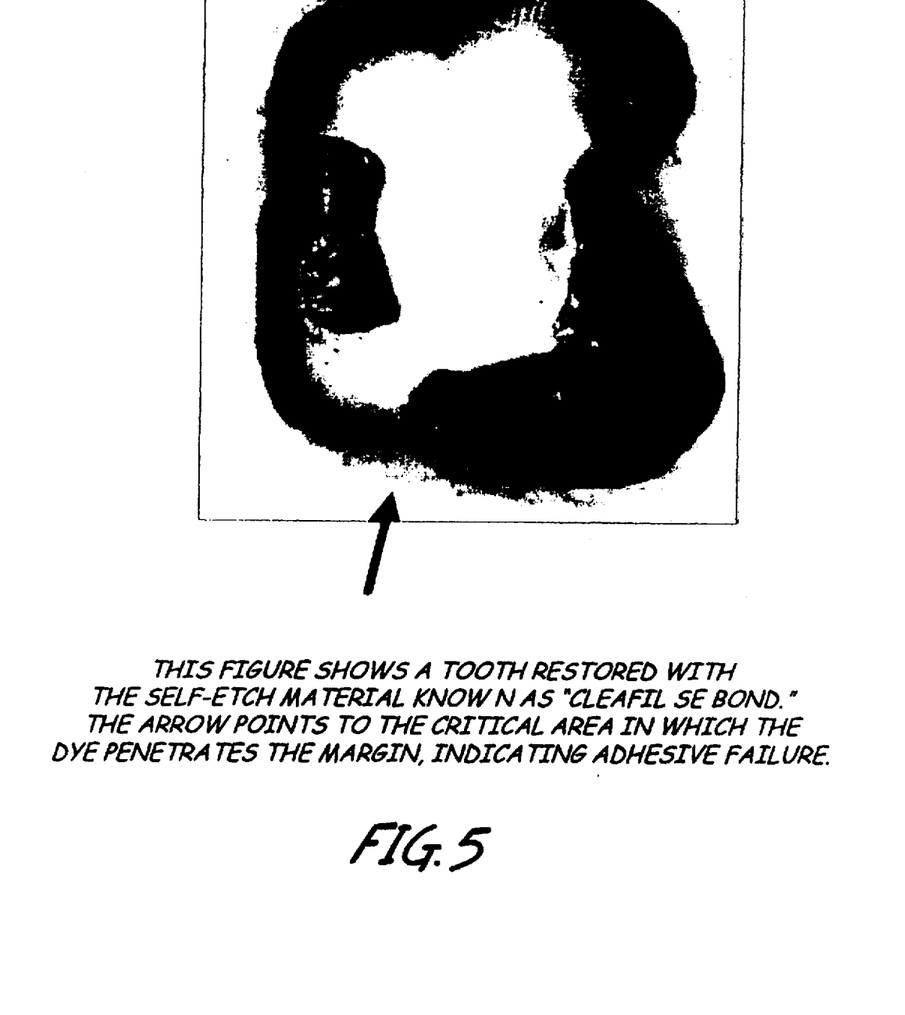
FIG. 5 is a cross sectional photograph of a tooth treated with "Clearfil SE Bond", a commercially available etch/bonding system. The arrow points to the critical area showing dye penetration into the tooth, indicating an adhesive failure at the margins of the treatment.

FIG. 5 is a cross sectional photograph of a tooth treated with "Clearfil SE Bond", a commercially available etch/bonding system. Clearfil SE Bond contains a phosphate ester and is available from Kuraray America, Inc., 200 Park Avenue, New York, N.Y. 10166-3098. The arrow points to the critical area showing dye penetration into the tooth, indicating an adhesive failure at the margins of the treatment.

FIGS. 1 and 2 demonstrate that the present invention provides superior adhesive properties such that dye does not penetrate the treated area by the method and compositions of the present invention. The commercially available etch/resin systems do not provide suitable adhesion such that the bonding of dental components is weak, thus allowing dye to penetrate into the poorly adhered portions of the tooth.

TABLE 1

| Inorganic Acid | Organic Acid | Dwell time | Substrate | mPA |
|---|---|---|---|---|
| 7% Nitric Acid | none | 30 seconds; no blotting | dentin; resin added without blotting | 12.21 ± 5.4 |
| 7% Nitric Acid | none | 30 seconds | enamel | 21.98 ± 3.2 |
| 7% Nitric Acid | succinic acid 5% | 30 seconds | dentin | 22.36 ± 1.4 |
| 7% Nitric Acid | succinic acid 5% | 30 seconds | enamel | 22.48 ± 1.2 |

The experiments in Table 1 were conducted with an etch solution having the concentration of ingredients listed in Table 1. The resin utilized was composed of 20% by weight of PMGDM, 15% by weight HEMA and 8% by weight of bis-GMA with the remainder being solvent. The method utilized was to apply the etch solution to the substrate surface with a cotton or foam pellet and gently agitate the solution soaked pellet against the substrate for approximately 10 to about 15 seconds. The pellet was then placed against an absorbent material such as a napkin or tissue to remove excess solution. The pellet was then contacted to the substrate surface to remove the excess etching solution by blotting (unless indicated otherwise). The resin composition was then applied to the substrate surface using 2 to 3 coats of the resin. This was dried thoroughly with dried compressed air for about 5 to about 8 seconds prior to treatment with a restorative material.

The applied resin was light-activated for ten seconds. A teflon mold having a matrix of 4 mm diameter and depth of 2 mm was clamped to the tooth. An all-purpose composite (quartz and silica composite material) was inserted into the matrix and light-activated for 40 seconds. The mold was then removed and the samples stored in water at 37 degrees C. for 24 hours. The samples were then subjected to shear bond strength testing on a Universal testing machine with a crosshead speed of 5 mm/min. The force required to break the composite from the surfaces was recorded in kg and converted to mPa on the basis of the surface area of the sample.

All samples throughout the experiments were prepared prior to testing. The test sample was steam sterilized for 24 hours prior to treatment. The preparation included that a tooth was stabilized and embedded into a cylindrical mounting with a polymerizable monomer, such as methyl methacrylate. The tooth surface was ground until an appropriate surface was exposed, i.e., enamel or dentin. The surface was finely polished, rinsed, dried and then treated. All samples were prepared this way; both with the etch and curable composites of the invention as well as those of competitive products. This was done for consistency between samples.

The following experiments were conducted with a composition of the present invention referred to as SIMPLICITY™. The etchant solution was composed of 5% by weight nitric acid, 2.5% by weight succinic acid and 2.5% by weight methacrylic acid, unless listed otherwise, with the balance being water. The resin was 20% by weight PMGDM, 15% by weight HEMA, 8% by weight bis-GMA, 3% by weight ethyldimethylaminobenzoic acid (EDMAB) and 0.3% by weight camphoroquinone (CQ), with the balance being acetone. Self cure means that the resin applied to the treated surface is self-cured, i.e., no light treatment. Light-activated systems were preferred as described above. To the resin treated surface was applied a restorative material identified in the chart. Additional light activation was utilized with the systems of the present invention.

In comparison, the protocols supplied by the commercial suppliers were utilized for the competitive products.

A teflon mold having a matrix of 4 mm diameter and depth of 2 mm was clamped to the sample tooth. The all-purpose composite or appropriate material was inserted into the matrix and treated as described above, or by the protocols supplied by the commercial supplier. The mold was then removed and the samples stored in water at 37 degrees C. for 24 hours. The samples were then subjected to shear bond strength testing on a Universal testing machine with a crosshead speed of 5 mm/min. The force required to break the composite from the surfaces was recorded in kg and converted to mPa on the basis of the surface area of the sample.

The method utilized was to apply the etch solution to the substrate surface with a cotton or foam pellet and gently agitate the solution soaked pellet against the substrate for approximately 10 to about 15 seconds. The pellet was then placed against an absorbent material such as a napkin or tissue to remove excess solution. The pellet was then contacted to the substrate surface to remove the excess etching solution by blotting. The resin composition was then applied to the substrate surface using 2 to 3 coats of the resin. This was dried thoroughly with dried compressed air for between about 5 and about 8 seconds and then light-activated for 10 seconds.

Light activation was achieved by use of a visible light generating device (Bisco VIP light, Bisco Dental Products, Schaumburg, Ill., that emits wavelengths approximately between about 400 and 500 nanometers (nm) (CQ absorption maximum is about 468 nm). Extra "air thinning" denotes that the resin applied was thinned by drying with compressed air for an extended period of time and with additional force. This causes oxygen inhibition to come into effect and provides for discrimination between those materials which are more susceptible to oxygen inhibition and those which are not.

The composite materials referred to include Bis-fil All Purpose, a quartz filled composite, B2FB is a self-cure composite available from Bisco Dental Products, Schaumburg, Ill., RelyX ARC is a dual-cure composite cement available from 3M Dental, St. Paul, Minn. and Z-100 is a restorative composite available from 3M. In order to compare the commercially available systems to that of the present invention, the method of testing on the final composite was maintained as the same throughout. Unless otherwise noted in the chart, composite samples were prepared with an all purpose quartz silica composite material for testing of adhesive/cohesive bond properties.

The following chart includes these abbreviations: DF denotes dental fracture. NP is a nonprecious metal, such as nickel chromium. Precious metal (ME) is a gold alloy.

| Instron | PSI | MPa | | |
|---|---|---|---|---|
| Group 84 | | | | |
| 1 | 35.4 | 4005.6 | 27.63 | |
| 2 | 39.5 | 4470.6 | 30.83 Simplicity | |
| 3 | 24.6 | 2781.7 | 19.18 enamel | |
| 4 | 31.1 | 3513.6 | 24.23 | |
| AVERAGE | 32.6 | 3692.9 | 25.47 | |
| ST. DEV | 6.4 | 722.3 | 4.98 | |
| CO. VAR., % | 19.6 | 19.6 | 19.6 | |
| Group 85 | | | | |
| 1 | 20.2 | 2289.6 | 15.79 Simplicity | Present invention with precious metal gold alloy (ME) |
| 2 | 23.0 | 2599.5 | 17.93 Precious metal | |
| 3 | 25.3 | 2866.5 | 19.77 metal | |
| 4 | 27.3 | 3082.6 | 21.26 (ME) | |
| AVERAGE | 24.0 | 2709.6 | 18.69 | |
| ST. DEV | 3.0 | 342.7 | 2.36 | |
| CO. VAR., % | 12.6 | 12.6 | 12.6 | |
| Group 86 | | | | |
| 1 | 28.2 | 3185.5 | 21.97 Simplicity | |
| 2 | 14.9 | 1688.9 | 11.65 BF2B | |
| 3 | 26.1 | 2946.8 | 20.32 dentin | |
| 4 | 20.4 | 2307.7 | 15.92 | |
| 5 | 28.6 | 3237.5 | 22.33 | |
| AVERAGE | 23.6 | 2673.3 | 18.44 | |
| ST. DEV | 5.9 | 663.0 | 4.57 | |
| CO. VAR., % | 24.8 | 24.8 | 24.8 | |
| | | | 20.13 | |
| | | | 2.94 | |
| | | | 14.6 | |
| Group 86-1 | | | | |
| 1 | 15.8 | 1788.5 | 12.33 Touch & Bond | Competing system with self-cure composite |
| 2 | 4.5 | 507.1 | 3.50 BF2B | |
| 3 | 6.1 | 695.5 | 4.80 dentin | |
| AVERAGE | 8.8 | 997.0 | 6.88 | |
| ST. DEV | 6.1 | 691.8 | 4.77 | |
| CO. VAR., % | 69.4 | 69.4 | 69.4 | |
| Group 86-2 | | | | |
| 1 | 14.5 | 1642.5 | 11.33 One-Up Bond | Competing system with self-cure composite |
| 2 | 6.3 | 710.6 | 4.90 BF2B | |
| AVERAGE | 10.4 | 1176.6 | 8.11 dentin | |
| ST. DEV | 5.8 | 659.0 | 4.54 | |
| CO.VAR., % | 56.0 | 56.0 | 56.0 | |
| Group 86-3 | | | | |
| 1 | 23.9 | 2702.5 | 18.64 Simplicity | |
| 2 | 24.0 | 2714.9 | 18.72 dentin | |
| 3 | 28.2 | 3185.5 | 21.97 | |
| 4 | 22.7 | 2572.4 | 17.74 | |
| 5 | 32.6 | 3690.0 | 25.45 | |
| AVERAGE | 26.3 | 2973.1 | 20.50 | |
| ST. DEV | 4.1 | 463.6 | 3.20 | |
| CO. VAR., % | 15.6 | 15.6 | 15.6 | |
| Group 86-4 unknown metal substrate | | | | |
| 1 | 19.7 | 2229.6 | 15.38 Simplicity | Present invention with non-precious metal Nickel/chromium |
| 2 | 20.5 | 2314.5 | 15.96 NP metal | |
| 3 | 25.7 | 2906.1 | 20.04 | |
| 4 | 29.4 | 3325.8 | 22.94 | |
| 5 | 22.4 | 2529.4 | 17.44 | |
| AVERAGE | 23.5 | 2661.1 | 18.35 | |
| ST. DEV | 4.0 | 454.3 | 3.13 | |
| CO. VAR., % | 17.1 | 17.1 | 17.1 | |
| Group 86-5 | | | | |
| 1 | 22.3 | 2527.1 | 17.43 SE Bond | Competing system with self-cure composite |
| 2 | 15.8 | 1786.2 | 12.32 BF2B | |
| 3 | 18.9 | 2134.6 | 14.72 | |
| AVERAGE | 19.0 | 2149.3 | 14.82 | |
| ST. DEV | 3.3 | 370.7 | 2.56 | |
| CO. VAR., % | 17.2 | 17.2 | 17.2 | |
| Group 86-6 | | | | |
| 1 | 23.0 | 2602.9 | 17.95 Simplicity | this shows the present invention bonds with self-cure composites |
| 2 | 18.7 | 2119.9 | 14.62 BF2B | |
| 3 | 27.5 | 3106.3 | 21.42 dentin | |
| AVERAGE | 23.1 | 2609.7 | 18.00 | |
| ST. DEV | 4.4 | 493.2 | 3.40 | |
| CO. VAR., % | 18.9 | 18.9 | 18.9 | |
| Group 86-7 | | | | |
| 1 | 23.4 | 2644.8 | 18.24 Simplicity | This shows the present system bonds well with another company's self-cure material |
| 2 | 19.1 | 2156.1 | 14.87 RelyX ARC | |
| 3 | 23.0 | 2602.9 | 17.95 dark cure | |
| 4 | 24.5 | 2776.0 | 19.14 dentin | |
| AVERAGE | 22.5 | 2545.0 | 17.55 | |
| ST. DEV | 2.4 | 269.5 | 1.86 | |
| CO. VAR., % | 10.6 | 10.6 | 10.6 | |
| Group 8 | | | | |
| 1 | 28.7 | 3248.9 | 22.41 | This is a control material "OS" is One Step |
| 2 | 37.9 | 4290.7 | 29.59 OS | |
| 3 | 34.5 | 3905.0 | 26.93 | |
| AVERAGE | 33.7 | 3814.8 | 26.31 | |
| ST. DEV | 4.7 | 526.7 | 3.63 | |
| CO. VAR., % | 13.8 | 13.8 | 13.8 Dentin fracture | |
| Group 9 | | | | |
| 1 | 25.1 | 2836.0 | 19.56 | |
| 2 | 34.2 | 3868.8 | 26.68 Simplicity | |
| 3 | 31.3 | 3538.5 | 24.40 enamel | |
| 4 | 23.3 | 2630.1 | 18.14 | |
| 5 | 24.0 | 2709.3 | 18.68 | |
| AVERAGE | 27.6 | 3116.5 | 21.49 | |
| ST. DEV | 4.9 | 553.4 | 3.82 | |
| CO. VAR., % | 17.8 | 17.8 | 17.8 | |
| Group 18 | | | | |
| 1 | 17.2 | 1946.8 | 13.43 | |
| 2 | 25.8 | 2915.2 | 20.10 | |
| 3 | 35.1 | 3975.1 | 27.41 DF | |
| 4 | 28.6 | 3239.8 | 22.34 Simplicity | |
| 5 | 25.9 | 2924.2 | 20.17 dentin | |
| AVERAGE | 26.5 | 3000.2 | 20.69 | |
| ST. DEV | 6.5 | 729.8 | 5.03 | |
| CO. VAR., % | 24.3 | 24.3 | 24.3 | |
| Group 19 | | | | |
| 1 | 33.6 | 3802.0 | 26.22 Simplicity | This shows the system works with other composites |
| 2 | 23.0 | 2599.5 | 17.93 Z100 | |
| 3 | 28.4 | 3216.1 | 22.18 dentin | |
| AVERAGE | 28.3 | 3205.9 | 22.11 | |
| ST. DEV | 5.3 | 601.3 | 4.15 | |
| CO. VAR., % | 18.8 | 18.8 | 18.8 | |

-continued

| Instron | PSI | MPa | | |
|---|---|---|---|---|
| Group 26 | | | | |
| 1 | 29.3 | 3316.7 | 22.87 | |
| | | | Simplicity | |
| 2 | 29.1 | 3295.2 | 22.73 | |
| 3 | 27.5 | 3115.4 | 21.49 | |
| AVERAGE | 28.7 | 3242.5 | 22.36 dentin | |
| ST. DEV | 1.0 | 110.6 | 0.76 | |
| CO. VAR., % | 3.4 | 3.4 | 3.4 | |
| Group 30 | | | | |
| 1 | 24.1 | 2724.0 | 18.79 | |
| | | | Simplicity | |
| 2 | 45.3 | 5126.7 | 35.36 | |
| | | | enamel | |
| 3 | 29.1 | 3291.8 | 22.70 | |
| 4 | 37.9 | 4288.5 | 29.58 | |
| 5 | 22.5 | 2547.5 | 17.57 | |
| AVERAGE | 31.8 | 3595.7 | 24.80 | |
| ST. DEV | 9.7 | 1092.6 | 7.53 | |
| CO. VAR., % | 30.4 | 30.4 | 30.4 | |
| Group 29 | | | | |
| 1 | 25.3 | 2860.9 | 19.73 | |
| | | | Simplicity | |
| 2 | 34.4 | 3893.7 | 26.85 dentin | |
| 3 | 23.4 | 2642.5 | 18.22 | |
| 4 | 29.0 | 3282.8 | 22.64 DF | |
| 5 | 32.0 | 3616.5 | 24.94 | |
| AVERAGE | 28.8 | 3259.3 | 22.48 | |
| ST. DEV | 4.6 | 517.1 | 3.57 | |
| CO. VAR., % | 15.9 | 15.9 | 15.9 | |
| Group 36 | | | | |
| 1 | 8.4 | 953.6 | 6.58 One-Up | 36, 37, 40 |
| 2 | 3.0 | 339.4 | 2.34 Bond | and 34 |
| 3 | 12.6 | 1420.8 | 9.80 air-thin | show how |
| AVERAGE | 8.0 | 904.6 | 6.24 5 sec | competing systems |
| ST. DEV | 4.8 | 542.4 | 3.74 dentin | suffer when |
| CO. VAR., % | 60.0 | 60.0 | 60.0 | thinned |
| | | | | with compressed |
| | | | | air. The present |
| | | | | system does not |
| | | | | suffer this drawback |
| Group 37 | | | | |
| 1 | 34.1 | 3856.3 | 26.60 | |
| | | | simplicity | |
| 2 | 29.4 | 3322.4 | 22.91 5 sec | |
| 3 | 22.2 | 2507.9 | 17.30 air thin | |
| AVERAGE | 28.5 | 3228.9 | 22.27 dentin | |
| ST. DEV | 6.0 | 679.1 | 4.68 | |
| CO. VAR., % | 21.0 | 21.0 | 21.0 | |
| Group 40 | | | | |
| 1 | 16.5 | 1871.0 | 12.90 | |
| | | | Touch & Bond | |
| 2 | 16.1 | 1822.4 | 12.57 5 sec | |
| 3 | 12.5 | 1409.5 | 9.72 air thin | |
| AVERAGE | 15.0 | 1701.0 | 11.73 dentin | |
| ST. DEV | 2.2 | 253.6 | 1.75 | |
| CO. VAR., % | 14.9 | 14.9 | 14.9 | |
| Group 34 | | | | |
| 1 | 9.2 | 1044.7 | 7.20 SE Bond | |
| 2 | 16.0 | 1810.0 | 12.48 5 sec | |
| 3 | 10.5 | 1187.8 | 8.19 air-thin | |
| 4 | 17.4 | 1970.6 | 13.59 resin | |
| 5 | 11.3 | 1278.3 | 8.82 dentin | |
| AVERAGE | 12.9 | 1458.3 | 10.06 | |
| ST. DEV | 3.6 | 407.1 | 2.81 | |
| CO. VAR., % | 27.9 | 27.9 | 27.9 | |

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

I claim:

1. A dental etching solution comprising
   nitric acid;
   an organic acid;
   a solvent; and
   water;
   wherein the nitric acid concentration is between about 6 and about 8 parts by weight, the organic acid is present in amount from about 0.01 to about 20 parts by weight, the solvent is present in an amount from about 1 to about 50 parts by weight, the water being present in an amount to equal a total of 100 parts by weight of all components.

2. The dental etching solution of claim 1, wherein the organic acid is selected from the group consisting of lactic acid, pyruvic acid, glycolic acid, chloroacetic acid, dichloroacetic acid, trichloroacetic acid, cyanoacetic acid, tartaric acid, succinic acid, glutaric acid, maleic acid, fumaric acid, malonic acid, citraconic acid, ortho-phthalic acid, meta-phthalic acid, para-phthalic acid, citric acid, tricarballyic acid, 1,3,5-pentanetricarboxylic acid and trimellitic acid.

3. The dental etching solution of claim 1, wherein the solvent is selected from the group consisting of acetone, dimethyl sulfoxide, and ethanol.

4. The dental etching solution of claim 3, wherein the solvent concentration is between about 10 and about 30 parts by weight.

5. The dental etching solution of claim 3, wherein the solvent is ethanol.

6. The dental etching solution of claim 5, wherein the solvent concentration is between about 10 and about 30 parts by weight.

7. A dental etching solution comprising
   an inorganic acid;
   succinic acid;
   a solvent; and
   water;
   wherein the inorganic acid is present in an amount of from about 1 to about 10 parts by weight, the succinic acid is present in amount from about 0.01 to about 20 parts by weight, the solvent is present in an amount from about 1 to about 50 parts by weight, the water being present in an amount to equal a total of 100 parts by weight of all components.

8. The dental etching solution of claim 7, wherein the succinic acid concentration is between about 1.0 and about 3.0 parts by weight.

9. The dental etching solution of claim 7, wherein the inorganic acid is selected from the group consisting of nitric acid, sulfuric acid, hydrochloric acid and phosphoric acid.

10. The dental etching solution of claim 7, wherein the solvent is selected from the group consisting of acetone, dimethyl sulfoxide, and ethanol.

11. The dental etching solution of claim 10, wherein the solvent concentration is between about 10 and about 30 parts by weight.

12. The dental etching solution of claim 11, wherein the solvent is ethanol.

13. The dental etching solution of claim 12, wherein the solvent concentration is between about 10 and about 30 parts by weight.

14. The dental etching solution of claim 7, further comprising an ethylenically unsaturated monomer.

15. The dental etching solution of claim 14, wherein the ethylenically unsaturated monomer is selected from the group consisting of ethyleneglycol acrylate phosphate, ethyleneglycol methacrylate phosphate, 2-hydroxyethylacrylate, 2-hydroxyethylmethacrylate, 2-hydroxypropylacrylate, 3-hydroxypropylacrylate, 2-hydroxypropylmethacrylate, 3-hydroxypropylmethacrylate, 1,3-dihydroxypropylacrylate, 2,3-dihydroxypropylacrylate, 1,3-dihydroxypropylmethacrylate, 2,3-dihydroxypropylmethacrylate, acrylic acid, methacrylic acid, 2-trimethylammonium ethylmethacrylic chloride, 2-acrylamido-2-methylpropane-sulfonic acid, 2-methacrylamido-2-methylpropane-sulfonic acid, acrylamide, methacrylamide, 2-hydroxyethylacrylamide, 2-hydroxyethylmethacrylamide, N,N-bis(2-hydroxyethyl)acrylamide, N,N-bis(2-hydroxyethyl)methacrylamide, N-alkyl-N-hydroxyethyl acrylamides, N-alkyl-N-hydroxyethyl methacrylamides, 2-hydroxypropylacrylamide, 2-hydroxypropylmethacrylamide, 3-hydroxypropylacrylamide, 3-hydroxypropylmethacrylamide, methacrylamidopropyltrimethylammonium chloride, gylcerol monomethacrylate and glycerol monoacrylate.

16. The dental etching solution of claim 14, wherein the ethylenically unsaturated monomer is present in an amount of from about 0.1 to about 10 parts by weight of the total of all components.

17. The dental etching solution of claim 14, wherein the ethylenically unsaturated monomer is methacrylic acid.

18. A dental etching solution comprising
an inorganic acid;
an organic acid;
ethyleneglycol methacrylate phosphate;
a solvent; and
water;
wherein the inorganic acid is present in an amount of from about 1 to about 10 parts by weight, the organic acid is present in amount from about 0.01 to about 20 parts by weight, the ethyleneglycol methacrylate phosphate is present in an amount from about 5 part to about 30 parts by weight, the solvent is present in an amount from about 1 to about 50 parts by weight, the water being present in an amount to equal a total of 100 parts by weight of all components.

19. The dental etching solution of claim 18, wherein the inorganic acid is selected from the group consisting of nitric acid, sulfuric acid, hydrochloric acid and phosphoric acid.

20. The dental etching solution of claim 18, wherein the organic acid is selected from the group consisting of lactic acid, pyruvic acid, glycolic acid, chloroacetic acid, dichloroacetic acid, trichloroacetic acid, cyanoacetic acid, tartaric acid, succinic acid, glutaric acid, maleic acid, fumaric acid, malonic acid, citraconic acid, ortho-phthalic acid, meta-phthalic acid, para-phthalic acid, citric acid, tricarballyic acid, 1,3,5-pentanetricarboxylic acid and trimellitic acid.

21. The dental etching solution of claim 18, wherein the solvent is selected from the group consisting of acetone, dimethyl sulfoxide, and ethanol.

22. The dental etching solution of claim 21, wherein the solvent concentration is between about 10 and about 30 parts by weight.

23. The dental etching solution of claim 22, wherein the solvent is ethanol.

24. The dental etching solution of claim 23, wherein the solvent concentration is between about 10 and about 30 parts by weight.

* * * * *